US006890581B2

(12) United States Patent
Vernon et al.

(10) Patent No.: US 6,890,581 B2
(45) Date of Patent: May 10, 2005

(54) METHODS FOR BUFFER STABILIZED AQUEOUS DEACYLATION

(75) Inventors: Nicholas M. Vernon, Daphne, AL (US); Edward Micinski, Martinez, GA (US); Steven J. Catani, Athens, GA (US); Juan L. Navia, Doylestown, PA (US)

(73) Assignee: Tate & Lyle Public Limited Company, London (GB)

( * ) Notice: Subject to any disclaimer, the term of this patent is extended or adjusted under 35 U.S.C. 154(b) by 421 days.

(21) Appl. No.: 10/116,758

(22) Filed: Apr. 5, 2002

(65) Prior Publication Data

US 2003/0190395 A1 Oct. 9, 2003

(51) Int. Cl.[7] .............................. A23G 3/00; C07H 1/06
(52) U.S. Cl. ...................... 426/658; 426/548; 536/124; 536/127
(58) Field of Search ................ 426/548, 658; 536/124, 127

(56) References Cited

U.S. PATENT DOCUMENTS

| | | | | |
|---|---|---|---|---|
| 4,362,869 A | | 12/1982 | Jenner et al. ................ 536/122 |
| 4,380,476 A | * | 4/1983 | Mufti et al. ................ 127/46.3 |
| 4,405,654 A | | 9/1983 | Lee ............................ 426/658 |
| 4,435,440 A | | 3/1984 | Hough et al. ............... 426/658 |
| 4,826,962 A | | 5/1989 | Rathbone et al. ........... 536/122 |
| 4,927,646 A | * | 5/1990 | Jenner et al. ................ 426/96 |
| 4,950,746 A | | 8/1990 | Navia ......................... 536/119 |
| 4,980,463 A | | 12/1990 | Walkup et al. ............. 536/124 |
| 4,980,473 A | | 12/1990 | Barton ........................ 546/10 |
| 5,023,329 A | | 6/1991 | Neiditch et al. ............ 536/119 |
| 5,034,551 A | | 7/1991 | Vernon et al. ............... 556/89 |
| 5,470,969 A | | 11/1995 | Sankey et al. .............. 536/115 |
| 5,498,709 A | | 3/1996 | Navia et al. ................ 536/124 |
| 5,530,106 A | | 6/1996 | Navia et al. ................ 536/4.1 |
| 5,932,720 A | * | 8/1999 | Sankey ....................... 536/124 |
| 5,977,349 A | | 11/1999 | Catani et al. ............... 536/124 |

FOREIGN PATENT DOCUMENTS

| | | |
|---|---|---|
| EP | 0 255 260 A | 2/1988 |
| EP | 0 409 549 A | 1/1991 |
| GB | 2 065 646 A | 7/1981 |

OTHER PUBLICATIONS

International Search Report dated Aug. 25, 2003.

* cited by examiner

*Primary Examiner*—Leslie Wong
(74) *Attorney, Agent, or Firm*—RatnerPrestia

(57) ABSTRACT

The present invention relates to novel methods for stabilizing aqueous deacylation, via use of buffers in the production of sucralose. The present invention provides a process for producing sucralose from an acyl-sucralose compound whereby the acyl-sucralose compound is deacylated in the presence of a buffering agent, which stabilizes the pH of the feed mixture and decreases the accumulation of undesired anhydro compounds. Further, the present invention provides a process whereby the acyl-sucralose compound is deacylated directly either prior to or after removal of the tertiary amide reaction vehicle from the neutralized chlorination feed mixture. An aqueous solution of sucralose including salts and other compounds is produced, from which sucralose is recovered by extraction and purified by crystallization.

22 Claims, No Drawings

METHODS FOR BUFFER STABILIZED AQUEOUS DEACYLATION

FIELD OF THE INVENTION

The present invention relates to novel methods for stabilizing aqueous deacylation, via use of buffers, in the production of sucralose. The present invention provides a process for producing sucralose from an acyl-sucralose compound whereby the acyl-sucralose compound is deacylated in the presence of a buffering agent, that stabilizes the pH of the feed mixture and decreases the accumulation of undesired anhydro compounds. Further, the present invention provides a process whereby the acyl-sucralose compound is deacylated directly either prior to or after removal of the tertiary amide reaction vehicle from the neutralized chlorination feed mixture. An aqueous solution of sucralose including salts and other compounds is produced, from which sucralose is recovered by extraction and purified by crystallization. The resultant sucralose has low levels of organic solvents.

BACKGROUND OF THE INVENTION

Selective modification of sucralose presents a major synthetic challenge because of the multiplicity of reactive —OH groups and the acid lability of the glycosidic linkage. When the target of interest is sucralose (4,1',6'-trichloro-4,1',6'-trideoxygalactosuccrose: in the process of making the compound, the stereo configuration at the 4 position is reversed; therefore, sucralose is a galacto-sucrose), the difficulty is compounded by a need to chlorinate the less reactive 4- and 1'-positions, while leaving intact the more reactive 6-position.

A number of different strategies for the preparation of sucralose have been developed to preblock the 6-position, usually by forming a sucralose-6-acylate such as sucralose-6-acetate and removing the blocking moiety as by hydrolysis after chlorination to produce sucralose. U.S. Pat. Nos. 4,950,746; 5,023,329; 5,034,551; 5,470,969; 4,362,869; 4,826,962; 5,470,969; 5,530,106; and 4,980,473, which are expressly incorporated by reference herein, relate to such strategies.

Prior to the isolation of pure sucralose, the sucralose-6-acylate is desterified by hydrolysis. In one approach, the ester groups are converted back to free hydroxyl groups by alkaline hydrolysis. After the hydrolysis, the feed mixture is adjusted to approximately neutral pH, and the sucralose is subsequently purified from the feed mixture by any one of several acceptable processes. See, e.g., the U.S. patent applications entitled "Extractive Methods for Purifying Sucralose" and "Process for Improving Sucralose Purity and Yield," filed 8 Mar. 2002, and expressly incorporated by reference herein. The de-esterification reaction may be carried in an organic system employing a material such as sodium methoxide that produces a transesterification reaction. In this case, the acid moiety forming the sucralose ester is converted to the methyl ester of the acid, whereby the methyl ester may be removed by distillation, driving the reaction to completion. Alternatively, the de-esterification reaction may be carried out in water under alkaline conditions, resulting in a base-mediated conversion of ester to sucralose and the salt of the acid that was used to form the ester. The latter use of an aqueous hydrolysis is desirable because it avoids the use of expensive solvents that must be removed during the later purification.

However, one problem with the latter sucralose purification strategy is that sucralose in the de-esterified form is unstable under intensely alkaline conditions and may be converted to undesirable compounds. For example, the anhydro compounds are undesirable because they decrease the overall reaction yield, and they affect the sweetness properties of sucralose. Hence, such undesirable compounds may also affect the duration of the extraction process. Moreover, high levels of such material greatly increase the difficulty of these purification steps.

The present invention provides processes whereby the acyl-sucralose compound is deacylated directly to produce an aqueous solution of sucralose including salts and other compounds, from which sucralose is recovered and preferably then purified by counter-current extraction, crystallization, or a combination of such techniques.

Accordingly, the present invention provides a sucralose purification process that produces sucralose compositions of enhanced purity and also minimizes the overall loss of sucralose during the purification process prior to any specific extraction, while reducing the formation of undesirable compounds such as anhydro sucralose.

SUMMARY OF THE INVENTION

The present invention provides a process for producing sucralose from a feed mixture comprising an acyl-sucralose compound in an aqueous solution, whereby the process comprises (a) adjusting the pH of the feed mixture; (b) maintaining the feed mixture at an appropriate temperature and time to effect the conversion of the acyl-sucralose compound into free sucralose; (c) adding a buffer to the feed mixture of step (b) to stabilize the pH; (d) decreasing the pH of the feed mixture of step (b); and (e) recovering free sucralose.

In one embodiment of the present invention sucralose may be produced from a feed mixture comprising an acyl-sucralose compound in an aqueous solution by adjusting the pH of the feed mixture to a range of about 8.0 to about 12.0; maintaining the feed mixture at an appropriate temperature for sufficient time to effect conversion of the acyl-sucralose compound into free sucralose; adding buffer to the feed mixture in an amount sufficient to stabilize the pH within the range for the duration of the maintaining step; decreasing the pH of the feed mixture to about 4 to about 8; and recovering the sucralose. In a specific embodiment, the pH of the feed mixture may be adjusted to about 10.5.

In one embodiment of the present invention, the buffer may be an amine, amino acid, phenol, inorganic acid, saccharin, xanthine, hydroquinine, or a mixture thereof. In another embodiment of the present invention, the amine may be ammonia, alkylamines R—NH2, dialkylamines R1R2NH, trialkylamines R1R2 R3N, wherein the R, R1, R2, R3 are methyl, ethyl, 1-propyl, 2-propyl, butyl, cyclohexyl, benzyl, pyrollidine or 2-hydroxypyridine. In yet another embodiment of the present invention, the amino acid may be glycine, alanine, arginine, dimethylglycine, cysteine, or a mixture thereof. In one embodiment of the present invention, the phenol may be phenol or resorcinol. In another embodiment, the inorganic acid may be a carbonate. In a specific embodiment of the present invention, the buffer may be dimethylamine or a salt of dimethylamine.

In another embodiment of the present invention, the acyl-sucralose compound may be 6-O-acyl-4,1',6'-trichloro-4,1',6'-trideoxygalactosuccrose. In yet another embodiment, the 6-O-acyl-4,1',6'-trichloro-4,1',6'-trideoxygalactosuccrose compound may be 6-O-acetyl-4,1',6'-trichloro-4,1',6'-trideoxygalactosuccrose. In still another embodiment, the 6-O-acyl-4,1',6'-trichloro-4,1',6'-trideoxygalactosuccrose compound may be 6-O-benzoyl-4,1',6'-trichloro-4,1',6'-trideoxygalactosucrose.

In an embodiment of the present invention, the feed mixture may be substantially free of a tertiary amide. In another embodiment the feed mixture may be substantially free of dimethylformamide.

In one embodiment of the present invention, the recovered sucralose may contain 20 ppm or less of an organic solvent. In this embodiment, the organic solvent may be methanol, ethanol, methyl acetate, toluene, pyridine, DMF, dichloromethane, chloroform, or a mixture thereof. In one embodiment, recovered sucralose may contain about 7 ppm or less of methanol. In another embodiment, recovered sucralose may contain about 7 ppm or less of ethanol. In yet another embodiment, recovered sucralose may contain about 10 ppm or less of methylacetate. In another embodiment, recovered sucralose may contain about 10 ppm or less of toluene. In one embodiment, recovered sucralose may contain about 20 ppm or less of DMF. In another embodiment, recovered sucralose may contain about 10 ppb or less of dichloromethane. In still another embodiment, recovered sucralose may contain about 10 ppb or less of chloroform.

One embodiment of the present invention may comprise a composition of matter comprising sucralose, wherein the sucralose comprises 20 ppm or less of an organic solvent. In this embodiment, the organic solvent may be methanol, ethanol, methyl acetate, toluene, pyridine, DMF, dichloromethane, chloroform, or a mixture thereof. In one embodiment, recovered sucralose may contain about 7 ppm or less of methanol. In another embodiment, recovered sucralose may contain about 7 ppm or less of ethanol. In yet another embodiment, recovered sucralose may contain about 10 ppm or less of methylacetate. In another embodiment, recovered sucralose may contain about 10 ppm or less of toluene. In one embodiment, recovered sucralose may contain about 20 ppm or less of DMF. In another embodiment, recovered sucralose may contain about 10 ppb or less of dichloromethane. In still another embodiment, recovered sucralose may contain about 10 ppb or less of chloroform. The present invention may also include a combination sweetener, a beverage, or a consumer product combined with sucralose.

One embodiment of the present invention may comprise a sucralose composition, wherein the sucralose has been deacylated and may contain about 20 ppm or less of an organic solvent. In this embodiment, the organic solvent may be methanol, ethanol, methyl acetate, toluene, pyridine, DMF, dichloromethane, chloroform, or a mixture thereof. In one embodiment, recovered sucralose may contain about 7 ppm or less of methanol. In another embodiment, recovered sucralose may contain about 7 ppm or less of ethanol. In yet another embodiment, recovered sucralose may contain about 10 ppm or less of methylacetate. In another embodiment, recovered sucralose may contain about 10 ppm or less of toluene. In one embodiment, recovered sucralose may contain about 20 ppm or less of DMF. In another embodiment, recovered sucralose may contain about 10 ppb or less of dichloromethane. In still another embodiment, recovered sucralose may contain about 10 ppb or less of chloroform. The present invention may also include a combination sweetener, a beverage, or a consumer product combined with sucralose.

Other objectives, features and advantages of the present invention will become apparent from the following detailed description. The detailed description and the specific examples, although indicating specific embodiments of the invention, are provided by way of illustration only. Accordingly, the present invention also includes those various changes and modifications within the spirit and scope of the invention that may become apparent to those skilled in the art from this detailed description.

DETAILED DESCRIPTION OF THE INVENTION

It is understood that the present invention is not limited to the particular methodologies, protocols, solvents, and reagents, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include plural reference unless the context clearly dictates otherwise. Thus, for example, a reference to "a solvent" is a reference to one or more solvents and includes equivalents thereof known to those skilled in the art and so forth.

Unless defined otherwise, all technical and scientific terms used herein have the same meanings as commonly understood by one of ordinary skill in the art to which this invention belongs. Numerous methods, devices, and materials are described herein, although any methods and materials similar or equivalent to those described herein can be used in the practice or testing of the present invention. All documents cited herein are incorporated by reference herein in their entirety.

Definitions

Batch operation as used herein describes a procedure in which a fixed amount of materials are introduced into a process, and the products obtained from this fixed amount of input are recovered prior to the addition of more input material.

Beverage as used herein includes any non-carbonated or carbonated beverage such as cola, diet cola, soda, diet soda, juice cocktail, root beer, birch beer, any fountain drink, sparkling fruit juice, water, sparkling water, tonic water, sport drink, fruit juices, isotonic beverages and club soda. Beverage may also include any fermented or non-fermented drink such as any beer, including ale, pilsner, lager, or derivation thereof, malt liquor, red wine, white wine, sparkling wine, fortified wine, wine cooler, wine spritzer, any pre-made cocktail mixer including margarita mix, sour mix, or daiquiri mix, any fermented fruit or tea beverage, hard liquor, and any flavored liqueur such as brandy, schnapps, bitters, or cordial. Beverage may include any liquid or dry dairy, milk, or cream product or any liquid or dry dairy, cream, or milk substitute such as half & half, non-dairy creamer, powdered creamer, flavored creamer, soy milk product, and lactose-reduced milk product and the like. Beverage may also include any fruit or vegetable juice in whole, concentrated, or powdered form and any combination of fruit and vegetable juices or other beverages. Beverage may also include coffee, any coffee drink, any coffee flavoring syrup, tea, iced tea, and cocoa, as well as any combination of any of the foregoing in powdered or liquid form. Beverage may also include powdered drink mixes of any flavors, including mixes requiring the addition of a sweetener before or after reconstitution to fluid form.

Blocked sucralose as used herein refers to sucralose molecules on which some or all of the remaining hydroxyl groups have been blocked by esterification or other means.

Combination sweetener as used herein includes any combination or permutation of sweeteners, including combinations of sucralose, saccharin, aspartame, acesulfame potassium, cyclamate, alitame, neotame, stevioside, glucose, fructose, levulose, maltose, lactose, any sugar alcohol, sorbitol, xylitol, and mannitol. Combination sweeteners may be granular in form, but may be in any other suitable form such as powder, liquid or syrup. The combination sweetener may consist essentially of sucralose. The combination sweetener may consist essentially of sucralose and a carrier such as dextrose, lactose, maltodextrin or water.

Consumer product as used herein includes fruit products such as applesauce, jams, jellies, marmalades, fruit snacks, fruit butters, and fruit spreads. Consumer product may also include any viscous or solid dairy, milk, or cream product, such as cheese, ice cream, ice milk, frozen yogurt, yogurt, and the like. Consumer product also includes baked goods such as breads, doughnuts, cakes, cheesecakes, danishes, pastries, pies, bagels, cookies, scones, crackers, muffins, and wafers. Consumer product includes cereal products such as ready-to-eat cold cereals, grits, hot cereals, granola mixes, oatmeal, and trail mixes. Consumer product includes condiments such as butter, peanut butter, whipped cream, dulce de leche, sour cream, BBQ sauce, chili, syrup, gravy, mayonnaise, olives, seasonings, relish, pickles, sauces, snack dips, ketchup, salsa, mustard, salad dressings, and pickled peppers. Consumer product includes snack foods and confectionary products such as apple bars, pudding, candy bars, hard candy, chocolate products, lollipops, fruit chews, marshmallows, chewing gum, bubble gum, gummy bears, jelly beans, caramel, taffy, pie fillings, syrups, gel snacks, mints, popcorn, chips, and pretzels. Consumer product includes meat products such as hot dogs, canned fish, sausage, prepared meats, canned meat, dehydrated meat, and luncheon meat. Consumer product includes soups, consommé, and bouillon. Consumer product includes dental products such as toothpaste, dental floss, mouthwash, denture adhesive, enamel whitener, fluoride treatments, and oral care gels. Consumer product includes cosmetic and beauty aids such as lipstick, lip balm, lip gloss, and petroleum jelly. Consumer product includes therapeutic items such as non-tobacco snuff, tobacco substitutes, pharmaceutical compositions, chewable medications, cough syrups, throat sprays, throat lozenges, cough drops, antibacterial products, pill coatings, gel caplets, soluble fiber preparations, antacids, tablet cores, rapidly absorbed liquid compositions, stable foam compositions, rapidly disintegrating pharmaceutical dosage forms, beverage concentrates for medicinal purposes, aqueous pharmaceutical suspensions, liquid concentrate compositions, and stabilized sorbic acid solutions, phosphate buffers, saline solutions, emulsions, non-aqueous pharmaceutical solvents (propylene glycol, polyethylene glycol, vegetable oils), aqueous pharmaceutical carriers (water, alcohol), and solid pharmaceutical carriers (lactose, cellulose), and pharmaceutical preservatives/additives (antimicrobials, antioxidants, chelating agents, inert gases, flavoring agents, coloring agents). Consumer product includes nutritional products such as meal replacement bars, meal replacement shakes, dietary supplements, protein mixes, protein bars, carbohydrate control bars, low carbohydrate bars, meal supplements, electrolyte solutions, whey protein products, metabolic response modifiers, appetite control beverages, and echinacea sprays. Consumer product includes animal foodstuffs such as dog and cat food, rat feed, cattle feed, pig feed, and bird feed. Consumer product includes foodstuffs such as baby food, infant formulae, and other products for infant health and nutrition, such as oral rehydration beverages. Consumer product includes tobacco products such as pipe tobacco, cigarette tobacco, and chewing tobacco. Consumer product includes any substance intended for oral consumption either alone or with another substance. Consumer product includes any composition intended for oral, parenteral, intravenous, subcutaneous, intramuscular, intraorbital, intraspinal, intrasternal, or intraarterial administration to a human or other animal such as livestock or a domestic animal. A consumer product may optionally include additional agents such as carriers (e.g., starch, lactose, and sucrose), bulking agents (e.g., maltodextrins), adjuvants (e.g., indocyanine green, vanilla, and oil of wintergreen), coloring agents, viscosity-adjusting agents including soluble cellulose derivatives (e.g., carboxymethylcellulose), thickening gums (e.g., xanthan, gellan, carrageenan), and synthetic food additive materials (e.g., polyoxyethylene, carbomer).

Continuous operation as used herein includes procedures in which product may be removed from the process while input may be added; removal of product or addition of input may be incremental, discontinuous, or at a constant rate. Those skilled in the art will readily recognize that many intermediate operations between pure batch operations and pure continuous processes are possible. The embodiments of the present invention may be readily practiced by this full range of possible operations.

Crude sucralose as used herein includes sucralose mixed with other chlorinated sugars, as well as sucralose and other chlorinated sugars on which some or all of the hydroxyl groups remaining after chlorination may have been blocked by esterification or other means known to those skilled in the art.

Crystallization as used herein includes processes in which a solution is rendered saturated or supersaturated with respect to a dissolved component, and the formation of crystals of this component is achieved. The initiation of crystal formation may be spontaneous, or it may require the addition of seed crystals. As used herein, crystallization also describes the situation in which a solid or liquid material is dissolved in a solvent to yield a solution that is then rendered saturated or supersaturated to obtain crystals. Also, included in the term crystallization are the ancillary processes of washing the crystals with one or more solvents, drying the crystals, and harvesting the final product obtained.

Extraction operation as used herein includes procedures that may be performed on a mother liquor to remove various compounds from the mother liquor. The specific operation may be selected from any number that may be suitable for removing undesirable compounds. These operations may include, but are not limited to, distillation, solvent extraction, chromatography, and derivatization followed by removal of the derivatized material.

Recycling of a mother liquor as used herein refers to the practice of adding the mother liquor to another sucralose solution prior to, or during, its crystallization. The mother liquor may be further concentrated or purified prior to recycling. Recovery of a substantial portion of the sucralose remaining in this mother liquor may be essential to achieving an economically acceptable process yield.

Solvent as used herein includes a liquid that can dissolve another substance.

In certain embodiments, "sucralose" may include compounds other than sucralose and includes products of any number of processes for synthesizing sucralose that are not sucralose. These include any monochloro-, dichloro-, tetrachloro-, and pentachloro-derivative of sucrose and any other dissacharide derived from sucrose, as well as any trichloro-derivative other than sucralose itself, whether present in free form or as esters of carboxylic acids. These include any halogenated sugar derivatives, such as dichlorosucrose acetate, 6,1',6'-trichlorosucrose, 4,6,6'-trichlorosucrose, 4,1',4',6'-tetrachlorogalactotagatose, 4,1',6'-trichlorogalactosucrose-6-acetate, 4,6,1',6'-tetrachlorogalactosucrose, 4,1'-dichlorogalactosucrose, 3',6'-dichloroanhydrosucrose, 4,6'-dichlorogalactosucrose, 1',6'-dichlorosucrose, 6,6'-dichlorosucrose, 4,1',6'-trichlorosucrose, 4,6,6'-trichlorogalactosucrose, 4,1',5'-trichlorogalactosucrose-6-acetate, and 4,6,6'-trichlorogalactosucrose and others as shown in U.S. Pat. Nos. 4,405,654; 4,435,440; 4,980,463; 5,034,551; 5,498,709; and 5,530,106. These include any organic or inorganic salt, carbohydrate, or acylated sucralose.

The present invention provides processes whereby acyl-sucralose compounds are deacylated directly to produce an aqueous solution of sucralose including salts and other compounds, from which sucralose is recovered. Sucralose may then be recovered by extraction, for example by using an organic solvent. The sucralose may then be purified by counter-current extraction, crystallization or a combination of both techniques. In one embodiment, the present invention provides a process for producing sucralose from a feed mixture comprising an acyl-sucralose compound in an aqueous solution.

In one embodiment, the process of the present invention comprises: (a) adjusting the pH of the feed mixture to the range of about 8 to about 11; (b) maintaining the feed mixture at an appropriate temperature and time to effect conversion of the acyl-sucralose compound into free sucralose; (c) adding a buffer to the feed mixture in an amount sufficient to stabilize the pH; (d) decreasing the pH of the feed mixture to about 4 to 8; and (e) recovering the sucralose. These steps may be performed in any appropriate order.

In one embodiment, the process of the invention may employ a feed mixture that may contain di-, tri-, and tetra-chlorinated sucralose compounds. U.S. Pat. No. 5,977,349, which is expressly incorporated by reference herein, relates to such mixtures and processes. In one embodiment of the present invention, the acyl-sucralose compound may comprise 6-O-acyl-4,1',6'-trichloro-4,1'6'-trideoxygalactosucrose esters. Further, the acyl-sucralose compound may comprise 6-O-acetyl-4,1',6'-trichloro-4,1'6'-trideoxygalactosucrose or 6-O-benzoyl-4,1',6'-trichloro-4,1'6'-trideoxygalactosucrose. The types of halogenated compounds present in this feed mixture may vary according to the synthetic route used and the particular conditions of the synthesis. Halogens suitable for use in the context of the present invention include bromine, chlorine, fluorine, and iodine. One skilled in the art may readily fill the various positions with the same halogen or with any combination or permutation of different halogens by methods known to those skilled in the art.

In addition to the acyl-sucralose compound, the present invention may employ a feed mixture that comprises at least one additional component selected from the group consisting of at least one other chlorinated sucrose different from said first chlorinated sucrose, salt and solvent. U.S. Pat. No. 4,980,463, which is expressly incorporated herein by reference relates to feed mixtures that may be the neutralized reaction product of the acyl-sucralose and that are also employed to purify sucralose. In that embodiment, the feed mixture contains acyl-sucralose (such as sucralose-6-acetate or sucralose-6-benzoate), most likely at least one other chlorinated sucrose (including esters thereof); the tertiary amide solvent for the chlorination reaction (preferably N,N-dimethylformamide); various salt by-products of the chlorination and neutralization reaction (including alkali, alkali earth metal, ammonium, and alkyl ammonium chlorides, for example, sodium chloride and dimethylamine hydrochloride, as well as alkali metal formates, such as sodium formate); and water.

Alternatively, the chlorination feed mixture can be subjected to steam stripping or the like to remove the tertiary amide solvent. U.S. Pat. No. 5,530,106, which is expressly incorporated herein by reference, relates to such processes. The removal of the tertiary amide may be followed by hydrolysis to remove the 6-acyl moiety to produce another feed mixture that can be used in the purification process of the invention. In this embodiment, the feed mixture used in the process of this invention may contain sucralose; possibly other chlorinated sucroses; various salt by-products of the chlorination and neutralization reaction (including alkali, alkali earth metal, ammonium and alkyl ammonium chlorides, for example, sodium chloride and dimethylamine hydrochloride, as well as alkali metal formates, such as sodium formate); water; less than about 1 or 2% by weight of the feed mixture of the tertiary amide solvent; and, some remaining sucrose-6-ester compounds (in an embodiment where the hydrolysis to remove the 6-acyl moiety was not complete).

On a laboratory scale, the crude chlorination product may be quenched in a batch operation by the addition (in one portion) of one molar equivalent (basis phosgene) of ice-cold aqueous solutions or slurries of the alkali or alkaline earth metal hydroxides. In one embodiment, the alkaline agents may include the hydroxides of sodium, potassium, and calcium. In a specific embodiment, more dilute aqueous alkaline solutions, such as about 3 to 4N sodium hydroxide, may be used. Broader ranges of concentration may also be used such as, about 2 to about 8N sodium hydroxide. At lower concentrations, precipitation of salts is reduced or avoided, which significantly reduces the amount of solids the process stream can accommodate. However, when the concentration becomes too low (e.g., below about 2N), the product stream may become diluted to an extent that may adversely affect the efficiency of the process.

In one method of practice of this quench method, a buffer may be added to cold aqueous alkali with vigorous stirring as rapidly as possible in a quantity sufficient to raise and maintain the pH to about 8 to about 10. The buffer of the present invention should provide protection against abrupt changes in alkalinity or acidity. After addition of the buffer, the solution may resist changes in pH when the solution is exposed to acids or alkalis that would otherwise cause dramatic changes in pH. In particular, the buffer of the present invention will maintain the concentration of hydrogen ions, $H^+$ at a fixed value.

In one embodiment of the present invention, the buffer should demonstrate good buffering activity at a pH of about 10.5. Further, the buffer should be capable of maintaining the pH of the solution within a range of 8 to 12.0. The addition of the buffer may prevent excursions of pH to higher levels that may cause a related increase in the production of undesired compounds. In an embodiment, other compounds may comprise the formation anhydro compounds, such as 3',6'-anhydro-4,1'-dichlorogalactosucrose and 1',2,3',6'-dianhydro-4-chlorogalactosucrose. Further, maintaining a closer control on the pH of the solution by the addition of buffer may standardize the purity profile and result in an improved reproducibility of the process of the present invention.

In one embodiment, the buffers of the present invention may include, but are not limited to, amines such as ammonia, alkylamines R—NH2, dialkylamines R1R2NH, trialkylamines R1R2R3N (where R, R1, R2, R3=methyl, ethyl, 1-propyl, 2-propyl, butyl, cyclohexyl, benzyl etc., heterocycles such as pyrollidine, 2-hydroxypyridine, etc; amino acids such as glycine, alanine, arginine, dimethylglycine, cysteine; phenols such as phenol, resorcinol, etc.; inorganic acids such as carbonate, and other buffers such as saccharin, xanthine, hydroquinone, or a mixture thereof. In another embodiment of the present invention, a suitable buffering agent may comprise dimethylamine or salts of dimethylamine.

After stirring several minutes at this mildly elevated pH, the quenched solution may be neutralized to pH 5–7 by the addition of an acid, such as, for example, concentrated aqueous hydrochloric acid or glacial acetic acid. The brief treatment of the quenched chlorination feed mixture at pH 8–10 may have the beneficial effect of insuring that the hydroxyl groups of the sucrose-6-ester that have not been replaced by chlorine atoms are returned to their original hydroxyl group form.

In an alternative embodiment, sufficient aqueous alkali and buffering agent may be added to attain a pH of 11 ($\pm$1) and held for sufficient time to remove the 6-acyl function and obtain sucralose in the presence of all the salts, residual tertiary amide (DMF), etc. However, some DMF may be lost by caustic hydrolysis to dimethylamine and sodium formate. For this reason, the deacylation prior to removal of DMF is less preferred, because it may be desirable to recover all the DMF for recycle and re-use.

DMF Removal

When sodium hydroxide is used in the quench step and the tertiary amide is DMF, the salts such as sodium chloride, dimethylamine hydrochloride and small amounts of sodium formate may be formed in the quench step. If the quench is continued with a deacylation by increasing the pH sufficient to effect deacylation, the extraction of sucralose from the quenched and thus deacylated product mixture may be complicated by the presence of DMF (or other tertiary amide) and the propensity of the tertiary amide to distribute between both organic and aqueous phases in the extraction step, which may be the logical next step in a process sequence for producing sucralose. The tertiary amide may dissolve sucralose in both phases, and may also tend to dissolve other materials present in both phases, which may make recovery of the sucralose in good yield difficult and/or expensive. Also, the presence of DMF or other tertiary amides may affect efficiency of sucralose purification by crystallization from the extraction solvent. A further probable complication may be the base-catalyzed decomposition of the tertiary amide. For all of these reasons, tertiary amides such as DMF are preferably removed prior to recovery and purification of the sucralose. Further, it is preferred to remove the DMF prior to the deacylation step.

For example, a steam stripping operation may be performed to remove a major proportion of the DMF (or other tertiary amide) in the quenched feed mixture (preferred mode) or in the quenched and deacylated feed mixture. In one embodiment, it may be desirable to remove at least 95%, and in a specific embodiment, from at least about 98 to 99.9%, of the DMF to limit such undesirable consequences.

Upon removal of the DMF (or other tertiary amide) by steam stripping, the DMF may be effectively replaced with water in the process stream and the DMF may be subsequently recovered from the aqueous overheads by distillation and may be recycled.

Sucralose-6-Ester Deacylation

In one embodiment of the present invention, the sucralose-6-ester is deacylated by increasing the pH of the feed mixture to about 11 ($\pm$1) at a temperature and for a period of time sufficient to effect the deacylation after removal of the tertiary amide. This step may be performed by adding sufficient alkali metal hydroxide, such as sodium hydroxide, with agitation, to increase the pH to the desired level. In addition, a buffering agent that demonstrates good buffering activity of a pH of about 10.5 may be added. In one embodiment, reaction times and temperatures within the range of about 30 minutes to 2 hours at about 15° C. to about 35° C. may be used. At the conclusion of the deacylation, the base present may be neutralized, as by addition of hydrochloric acid, to a pH of about 5 to 7. After neutralization, the aqueous feed mixture may contain sucralose, salts (as above, plus the salt produced by the neutralization step described immediately above), and other chlorinated sucrose byproducts.

Sucralose Extraction

Following deacylation, sucralose may be isolated by extraction of the aqueous brine solution with a variety of organic solvents. These solvents include methyl acetate, ethyl acetate, methyl ethyl ketone, methyl iso-butyl ketone, methyl iso-amyl ketone, methylene chloride, chloroform, diethyl ether, methyl tert-butyl ether, and the like. U.S. patent application entitled "Extractive Methods for Purifying Sucralose" relates to such processes. In a specific embodiment, ethyl acetate may be used for reasons of extraction selectivity, ease of recycle, and toxicological safety.

Sucralose isolation may be performed in the laboratory by first partially evaporating the crude neutralized deacylation reaction product. About half the water present may optionally be removed, producing a solution containing about 2 to 5 wt % carbohydrates and about 15 to 25 wt percent salts. Isolation may be performed by carrying out three sequential extractions with ethyl acetate or other appropriate solvent. The extracts may be combined, and may optionally be washed with water (to partially remove any residual DMF and dichlorodideoxysucrose derivatives that to some extent are partitioned into the organic phase).

In addition to the batch extraction technique outlined above, extraction may also be carried out continuously on the dilute (not concentrated by evaporation) stream in a counter current mixersettler extraction system. The advantage is that no prior evaporation-concentration step is required. Such counter-current extraction techniques are known in the art.

Once the crude sucralose has been recovered from the aqueous brine as a solution in an appropriate organic solvent, it is concentrated and the product can be purified by crystallization and recrystallization from the same solvent until the required purity is achieved. U.S. patent application entitled "Process for Improving Sucralose Purity and Yield" relates to such processes. Alternatively, the sucralose may be crystallized from a solvent mixture such as methanol-ethyl acetate or from water to achieve the desired purity level. Sequential partitioning of the sucralose between solvent-water mixtures in a counter-current manner may also allow a purification to be achieved and likewise allows a direct liquid fill process, i.e., no material isolation may be needed because the final process stream may have the requisite specifications to be directly packaged for use.

Another embodiment of the purification/recovery process described above is that the same solvent may be used for both extraction and purification steps. Typically, i.e., with other chemical materials, it is unlikely that the chemical product to be purified will crystallize from the same solvent that is used for extraction. In the present case, however, a combination of dilution and relatively low levels of other compounds may allow the sucralose to remain in solution during the extraction, and then after the solution containing the extracted sucralose is concentrated, the sucralose product may then be crystallized from the same solvent.

Another aspect of the present invention relates to sucralose, produced via the methods and processes disclosed herein, and including the disclosed deacylation, crystallization and extraction techniques, which contains low levels of organic solvent. Such solvents may include, for example, methanol, ethanol, methylacetate, toluene, pyridine, DMF, dichloromethane, chloroform, and any combination thereof. In a specific embodiment, levels of solvent in the sucralose may be less that 20 ppm. In particular, levels of methanol or ethanol may be 7 ppm or less. In another embodiment, levels of methylacetate, toluene, or pyridine may be 10 ppm or less. In another embodiment, the level of DMF present in the sucralose may be 20 ppm or less. In still another embodiment, the level of dichloromethane or chloroform in the sucralose may be 10 ppb or less.

The levels of such solvents in sucralose can be measured by known methods, such as gas chromatography for example, and as shown in Table 1. Organic solvents that may be tested include methanol, ethanol, methylacetate, toluene, pyridine, DMF, dichloromethane, chloroform or a mixture thereof.

TABLE 1

| Organic Solvent | Level |
| --- | --- |
| Methanol | 7 ppm |
| Ethanol | 7 ppm |
| Methylacetate | 10 ppm |
| Toluene | 10 ppm |
| Pyridine | 10 ppm |
| DMF | 20 ppm |
| Dichloromethane | 10 ppb |
| Chloroform | 10 ppb |

The sucralose produced by the present invention may be used in beverages, consumer products, combination sweeteners and other such products.

EXAMPLES

Example 1

Limiting Production of Anhydro Compounds with Addition of Buffering Agent

A solution containing acetyl-6-O-4,1',6'-trichloro-4,1',6'-trideoxygalactosucrose (or, 6-acetyl ester) was prepared as related in U.S. Pat. No. 5,977,349, which is expressly incorporated by reference herein. Steam stripping was employed to remove any dimethylformamide remaining from the synthetic reaction. The feed mixture contained, in addition to the acetyl-6-ester, other chlorinated sucrose derivatives, residual N,N-dimethylformamide, salt byproducts of the chlorination and neutralization reactions, including alkali, ammonium, and alkyl ammonium chlorides. Sodium chloride was a significant portion of the products, and dimethylamine hydrochloride was also present.

Sufficient aqueous sodium hydroxide was added to raise the pH of the feed mixture to about 10.5. This pH was sufficient to facilitate the alkaline hydrolysis of the acetyl-6-ester. Concurrently with the caustic, dimethylamine hydrochloride was added to provide buffer capacity to prevent an excessive increase in pH, which causes the formation of undesirable anhydro sucralose derivatives. The above conditions were sufficient to substantially convert the acetyl-6-ester to sucralose. A broad range of reaction conditions can be used to effect this reaction.

What is claimed is:

1. A process for producing sucralose from a feed mixture comprising an acyl-sucrose compound in an aqueous solution, wherein said process comprises:

(a) adjusting the pH of said feed mixture to a range of about 8.0 to about 12.0;

(b) maintaining said feed mixture at an appropriate temperature for sufficient time to effect conversion of said acyl-sucralose compound into free sucralose;

(c) adding a buffer to said feed mixture in an amount sufficient to stabilize said pH within said range for the duration of said maintaining step;

(d) decreasing said pH of said feed mixture to about 4 to about 8; and (e) recovering sucralose from the product of step (d), thereby obtaining a recovered sucralose.

2. The process of claim 1, wherein said pH is about 10.5.

3. The process of claim 1 wherein said buffer is selected from the group consisting of amines, amino acids, phenols, inorganic acids, saccharin, xanthine, hydroquinine, and a mixture thereof.

4. The process of claim 3, wherein said amines are selected from the group consisting of ammonia, alkylamines $RNH_2$, dialkylamines $R1R2NH$, trialkylamines $R1R2 R3N$, wherein R, R1, R2, and R3 are selected from the group consisting of methyl, ethyl, 1-propyl, 2-propyl, butyl, cyclohexyl, benzyl, pyrrolidinyl, and 2-hydroxypyridyl.

5. The process of claim 3, wherein said amino acids are selected from the group consisting of glycine, alanine, arginine, dimethylglycine, cysteine, and a mixture thereof.

6. The process of claim 3, wherein said phenols are selected from the group consisting of phenol and resorcinol.

7. The process of claim 3, wherein said inorganic acid is a carbonate.

8. The process of claim 1, wherein said buffer is dimethylamine or a salt of dimethylamine.

9. The process of claim 1 wherein said acyl-sucralose compound is a 6-O-acyl-4,1',6'-trichloro-4,1',6'-trideoxygalactosucrose compound.

10. The process of claim 9, wherein said 6-O-acyl-4,1',6'-trichloro-4,1',6'-trideoxygalactosucrose compound is 6-O-acetyl-4,1',6'-trichloro-4,1',6'-trideoxygalactosucrose.

11. The process of claim 9, wherein said 6-O-acyl-4,1',6'-trichloro-4,1',6'-trideoxygalactosucrose compound is 6-O-benzoyl-4,1',6'-trichloro-4,1',6'-trideoxygalactosucrose.

12. The process of claim 1 wherein said feed mixture is substantially free of a tertiary amide.

13. The process of claim 1 wherein said feed mixture is substantially free of dimethylformamide.

14. The process of claim 1, wherein said recovered sucralose contains about 20 ppm or less of an organic solvent.

15. The process of claim 14, wherein said organic solvent is selected from the group consisting of: methanol, ethanol, methyl acetate, toluene, pyridine, DMF, dichloromethane, chloroform, and a mixture thereof.

16. The process of claim 15, wherein said recovered sucralose contains about 7 ppm or less of methanol.

17. The process of claim 15, wherein said recovered sucralose contains about 7 ppm or less of ethanol.

18. The process of claim 15, wherein said recovered sucralose contains about 10 ppm or less of methyl acetate.

19. The process of claim 15, wherein said recovered sucralose contains about 10 ppm or less of toluene.

20. The process of claim 15, wherein said recovered sucralose contains about 20 ppm or less of DMF.

21. The process of claim 15, wherein said recovered sucralose contains about 10 ppb or less of dichloromethane.

22. The process of claim 15, wherein said recovered sucralose contains about 10 ppb or less of chloroform.

* * * * *

UNITED STATES PATENT AND TRADEMARK OFFICE
CERTIFICATE OF CORRECTION

PATENT NO. : 6,890,581 B2
DATED : May 10, 2005
INVENTOR(S) : Vernon et al.

It is certified that error appears in the above-identified patent and that said Letters Patent is hereby corrected as shown below:

Column 2,
Line 48, delete "hydroquinine" and insert therefore -- hydroquinone --.

Column 12,
Line 30, delete "hydroquinine" and insert therefore -- hydroquinone --.
Line 34, delete "R1R2 R3N" and insert therefore -- R1R2R3N --.

Signed and Sealed this

Sixteenth Day of August, 2005

JON W. DUDAS
*Director of the United States Patent and Trademark Office*